United States Patent [19]

Mühlbauer

[11] Patent Number: 5,800,169
[45] Date of Patent: Sep. 1, 1998

[54] SUPPLY AND METERING SYRINGE FOR VISCOUS DENTAL COMPOUNDS

[76] Inventor: Ernst Mühlbauer, Elbgaustrasse 248, 22547 Hamburg, Germany

[21] Appl. No.: 789,062

[22] Filed: Jan. 28, 1997

Related U.S. Application Data

[63] Continuation of Ser. No. 350,489, Dec. 7, 1994, abandoned.

[30] Foreign Application Priority Data

Dec. 10, 1993 [DE] Germany .............. 93 19 007 U

[51] Int. Cl.⁶ .................................................. A61C 5/04
[52] U.S. Cl. ................................................ 433/90; 433/226
[58] Field of Search ............................... 433/89, 90, 226

[56] References Cited

U.S. PATENT DOCUMENTS

| | | | |
|---|---|---|---|
| 833,044 | 10/1906 | Goodhugh | 433/90 |
| 1,694,524 | 12/1928 | Zentner | 241/286 |
| 2,752,920 | 7/1956 | Kurkjian | 604/218 |
| 3,227,161 | 1/1966 | Lorenzo | 604/218 X |
| 3,611,573 | 10/1971 | Crawford et al. | 433/90 X |
| 3,823,715 | 7/1974 | Holanek et al. | 604/218 X |
| 4,551,135 | 11/1985 | Gorman et al. | 604/82 |
| 4,758,158 | 7/1988 | Pierce et al. | 433/90 |
| 4,798,596 | 1/1989 | Mühlbauer | 604/218 |
| 4,820,278 | 4/1989 | Balisky | 604/218 |
| 4,952,209 | 8/1990 | Mühlbauer | 604/218 |
| 5,122,057 | 6/1992 | Discko, Jr. | 433/90 |
| 5,547,379 | 8/1996 | Hasel | 433/212.1 |

FOREIGN PATENT DOCUMENTS

| | | | |
|---|---|---|---|
| 0006545 | 1/1980 | European Pat. Off. | 604/218 |
| 0 006 545 A2 | 10/1980 | European Pat. Off. . | |
| 0 106 053 A1 | 10/1983 | European Pat. Off. . | |
| 0 106 053 A1 | 4/1984 | European Pat. Off. . | |
| 0106053 | 4/1984 | European Pat. Off. | 433/90 |
| 0 284 244 A1 | 9/1988 | European Pat. Off. . | |
| 0 400 404 A1 | 12/1990 | European Pat. Off. . | |
| 1191538 | 10/1959 | France . | |
| WO 93/16653 A1 | 9/1993 | WIPO . | |

Primary Examiner—Robert P. Swiatek
Assistant Examiner—Elizabeth Shaw
Attorney, Agent, or Firm—Alix, Yale & Ristas, LLP

[57] ABSTRACT

A supply and metering syringe for viscous dental compounds, having a syringe body which contains a piston and opens out in a delivery opening. The delivery opening adjoins the syringe body without a constriction. As a result, a separation of the compound components in the surface region of the emerging strand is prevented. The diameter of the syringe body preferably widens toward the delivery opening.

6 Claims, 2 Drawing Sheets

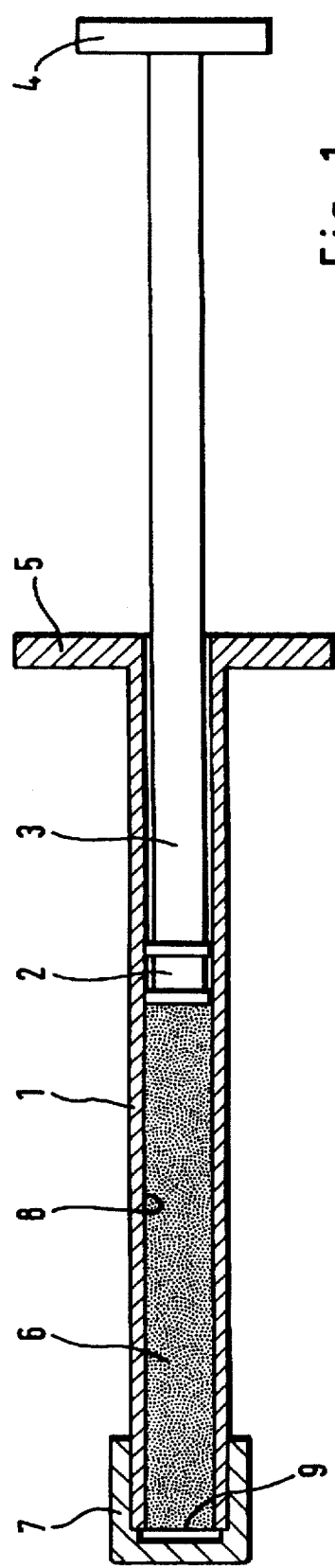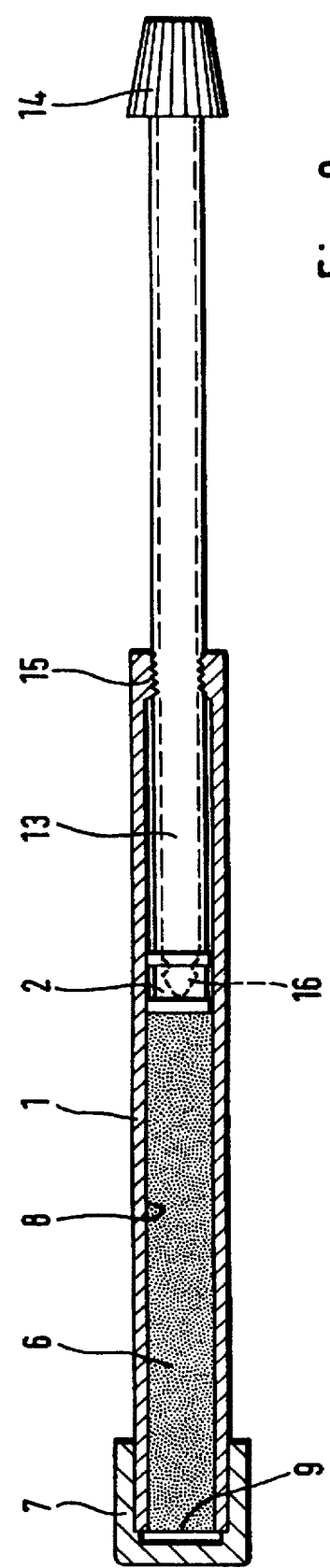

SUPPLY AND METERING SYRINGE FOR VISCOUS DENTAL COMPOUNDS

This application is a continuation of application Ser. No. 08/350,489 filed on Dec. 7, 1994 and now abandoned.

BACKGROUND AND SUMMARY OF THE INVENTION

The invention relates to a supply and metering syringe for a viscous dental compound, having a syringe body which has a bore which contains a piston and opens out into a delivery opening.

Viscous dental compounds are primarily understood to be greatly filled resins which are intended for fillings and for coverings on natural teeth and false teeth. This entire scope of application is meant when, for reasons of simplicity, only fillings are mentioned below. The dental compounds consist of a high proportion of filler material and a thin-liquid to honey-like resin phase which, in turn, can consist of a plurality of components of different viscosity. Although the dental compounds are extremely viscous, they are in any case capable of flow due to the liquid resin proportion. This distinguishes them from amalgam which, even in the plastic state, is never liquid.

To store, provide and meter these compounds, syringes are used, whose syringe body contains the compound in a cylindrical bore. By means of a piston, the compound can be squeezed through a delivery opening. This delivery opening generally has a diameter of a few millimeters. The syringe body and the piston have a larger diameter so that the required volume can be accommodated in a moderate length of the syringe body. The larger the diameter in the supply part of the application syringe is, the more dental compound can be stored therein; the smaller the delivery opening is, the greater the target accuracy with which the compound can be applied. In the known syringes, there is thus always a constriction between the bore of the syringe body and the delivery opening. Although it is known that it may be expedient in respect of the delivery forces to keep the area ratio between the syringe body and the delivery opening small (EP-B-0,220,551), the constriction would never be dispensed with. This is also not necessary due to the capability of the compound to flow.

The inventor has recognized that, when delivering viscous filling compounds from the known supply syringes, certain changes take place on the surface of the strand squeezed out, which can have adverse effects. He has observed that, after the strand has emerged, the surface is initially rough and cracked, and he has discovered upon closer examination that this is associated with separation phenomena between the phases of different consistency contained in the compound. On the one hand, the separation phenomena result in some areas in deviations from the desired composition ratio. On the other hand, due to the roughness and cracking of the surface of the emerging strand, air entrapments may result, which remain in the compound and in the tooth filling produced therefrom and lead to defects. Furthermore, he has discovered that these phenomena originate from the particular flow conditions to which the compound is subjected during delivery from the syringe with a simultaneous reduction in its cross section.

The invention therefore consists in the teaching of avoiding a deterioration in quality of the strand emerging from the syringe by the bore of the syringe being designed without a constriction up to its delivery opening.

Application tubes without a constriction are known for amalgam (WO-93/16653, FR-A-1,191,538, U.S. Pat. No. 1,694,524). The dentist mixes the amalgam separately, transfers lumps of the mixed amalgam to the application tube and applies it therewith in the tooth cavity to be filled. It is obvious that amalgam application tubes of this type must be without constrictions for three reasons. On the one hand, this is necessary because the lumps of amalgam to be applied are introduced into the application tube through the delivery opening. On the other hand, the consistency of the amalgam which is incapable of flow prohibits any constriction. There was no reason to transfer the constriction-free shape of the application tubes intended for amalgam to the application syringes intended for viscous resin compounds because this would have been disadvantageous, according to the finding of the person skilled in the art, for the reasons specified above. He could not know that the lack of constriction for a dental compound capable of flow, in contrast to amalgam, leads to an improvement in quality of the material emerging from the application syringe. The invention could not be suggested by the known amalgam application tubes since, with the latter, the lack of constriction is based on other aspects and the teaching cannot be taken from these aspects that a lack of constriction leads to an improvement in quality in the case of resin compounds capable of flow.

A further improvement in accordance with the invention can be achieved by the clear diameter of the syringe bore being widened slightly toward the delivery opening. As a result, the friction of the moving strand on the syringe wall is reduced or partially eliminated with the result that the laminar velocity differences and thus the shearing stresses in the moving strand and the resultant tendency to a segregating movement of its components are avoided completely.

Since the lack of constriction and any widening of the syringe body is associated with a reduction in the delivery forces, manual force is often sufficient to advance the piston. However, it may be advantageous to enlarge the piston force by means of a stepping-down device, for example a threaded spindle. In respect of the desirable size of the delivery opening, the diameter of the syringe bore and of the piston is expediently smaller than in known supply syringes so that, for this reason too, the delivery force is reduced. The diameter mentioned is expediently in the order of magnitude of 3 to 6 mm, preferably 4 to 5 mm.

The syringe according to the invention preferably takes up a filling volume which is sufficient for many applications. However, it is also possible to restrict the filling volume to a single requirement. It is then expediently designed in such a way that it can be coupled to a suitable applicator.

BRIEF DESCRIPTION OF THE DRAWINGS

The invention is explained in greater detail below with reference to the drawing which illustrates advantageous exemplary embodiments and in which:

FIG. 1 shows a longitudinal section through a supply syringe with manual advance of the piston;

FIG. 2 shows an embodiment of the syringe according to FIG. 1 fitted with a threaded spindle;

DESCRIPTION OF A PREFERRED EMBODIMENT

Figure 3:
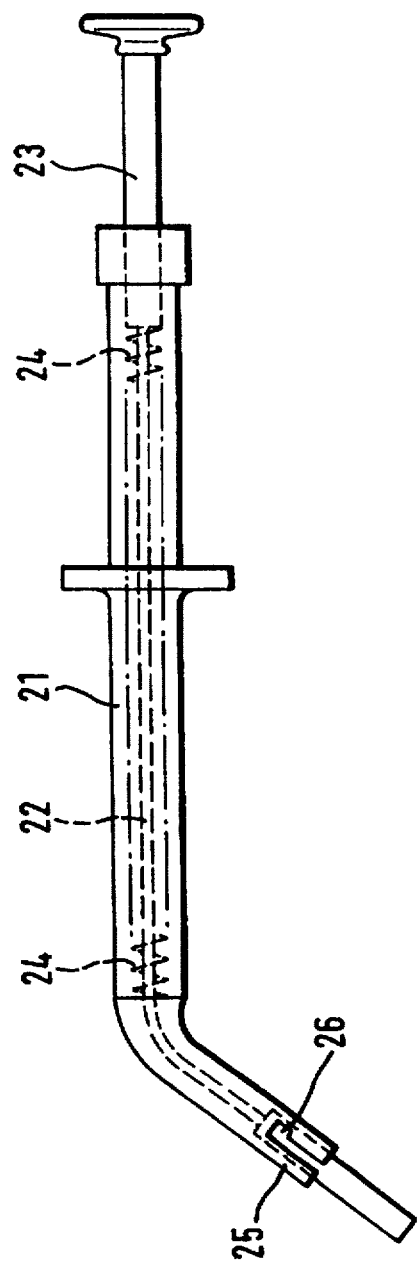
FIG. 3 shows an applicator with a syringe capsule.

In the design according to FIG. 1, there is located in the bore 8 of the essentially cylindrical syringe body 1 the piston 2 which can be advanced by means of a piston rod 3 which can but does not have to be joined integrally to the piston 2. For this purpose, there is located, at the end of the piston rod 3, a handle 4 for the thumb and, on the syringe body 1, an abutment 5 for the middle finger and index finger of the hand actuating the syringe. The compound 6 is located in the bore 8 of the syringe body 1, which bore has a clear diameter in the order of magnitude of 5 mm which becomes constantly larger from the back to the front toward the delivery opening 9 by a few tenths of a millimeter, for example by 0.1 to 0.2 mm. The delivery opening 9 can be closed by a cap 7. The length of the syringe body is about 7 to 8 cm for example. A quantity of the filling compound can therefore be accommodated, which is sufficient for a multiplicity of fillings. The compound can easily be provided and metered from the syringe since the advancing force is sufficiently small for manual actuation. By virtue of the viscosity of the compound, the advance is even.

The exemplary embodiment according to FIG. 2 differs from that according to FIG. 1 in that the piston rod is constructed as a threaded spindle 13 whose thread interacts with a nut thread 15 at the rear end of the syringe body 1. The handle on the syringe body for manual actuation is missing. Provided at the rear end of the spindle is an actuating part 14, by means of which the spindle can be turned. The spindle 13 is a part which is separate from the piston 2. At its front end it has a catch member 16 which can be engaged securely against tension in an undercut bore in the piston so that the piston can be retracted by turning the spindle in the opposite direction to advancing. This is advantageous so that some of the expensive compound which was possibly delivered beyond the quantity of momentary requirement can be sucked back into the syringe.

Figure 4:
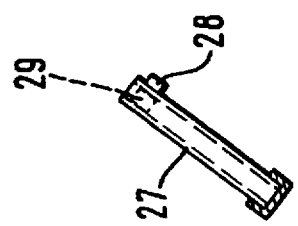
FIG. 4 shows the syringe capsule used in the exemplary embodiment according to FIG. 3.

If the filling volume of the syringe is limited to the quantity which is sufficient for one requirement, very small syringe bodies are arrived at, such as are illustrated in FIG. 4 and which are described here as syringe capsules. Since it would be very expensive to fit such a syringe capsule with actuating devices, they are expediently used in conjunction with a so-called applicator, such as is illustrated in FIG. 3. The latter has an elongate, hollow-cylindrical body 21 in which a flexible rod 22 can be advanced by means of a handle 23 counter to the force of a spring, such as is indicated at 24. At the front end which is expediently curved in the shape illustrated, the applicator forms a nozzle 25 which is provided with a bayonet cutout 26. The tubular nozzle 25 has an inside diameter which is slightly larger than the outside diameter of the syringe capsule 27 which has, at its rear end, a lateral bayonet projection 28 which fits into the bayonet recess 26 in the nozzle 25. In the starting condition, the front end of the flexible rod 22 lies in the nozzle 25 centrally behind the syringe capsule 27. When it is advanced by pressure on the actuating device 23, it presses the piston 29 of the syringe capsule forwards, as a result of which the latter is emptied. The bore of the syringe capsule 27 is likewise cylindrical or widens toward its mouth opening as was described above.

What is to be understood by a viscous compound and its viscosity or capability of flow will become clear in the following example. A strand which is round in cross section having a diameter of 5 mm and a length of 10 mm is delivered on a horizontal surface. After half an hour, the strand still has an approximately circular cross section. However, its underside resting on the bearing surface has become flattened over a width of about 2 mm.

I claim:

1. A process for dispensing a strand of a viscous, flowable dental compound with a syringe comprising the steps of providing a syringe body having a bore for the dental compound opening out to a delivery opening without a constriction therebetween, the syringe body being a capsule having the capacity of a single application of the dental compound and having a coupling device for connection to an applicator, providing a piston movable within said bore including an applicator housing the piston, the applicator having coupling means cooperating with the coupling device for mounting the capsule to the applicator, mounting the capsule to the applicator prior to advancing the piston and advancing the piston along the bore for dispensing the dental material therein through the delivery opening without constricting the dental compound and thereby forming the strand of the dental compound.

2. The process of claim 1 wherein the bore widens slightly toward the delivery opening to reduce the friction between the syringe body and the dental compound.

3. The process of claim 1 wherein the piston is advanced up to the delivery opening.

4. The process of claim 1 wherein the piston is advanced by hand.

5. The process of claim 1 including the step of providing a piston rod connected to the piston wherein the piston rod and the applicator are threadably connected and rotating the rod relative to the applicator to advance the piston.

6. The process of claim 1 including the step of providing a piston rod connected to the piston whereby the rod is subjected to tensile loading upon retraction of the piston for drawing the dental compound into the bore.

* * * * *